United States Patent [19]

De Jong

[11] Patent Number: Plant 6,719

[45] Date of Patent: Apr. 4, 1989

[54] BOUVARDIA NAMED ROXANNE

[76] Inventor: John M. F. De Jong, Floraweg 67, 2371 AM Roelofarendsveen, Netherlands

[21] Appl. No.: 127,100

[22] Filed: Dec. 1, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Jackson & Jones

[57] ABSTRACT

A new Bouvardia variety characterized by the cherry pink, double flowers. The blooms have a better stem quality, and a longer vase life.

1 Drawing Sheet

BACKGROUND OF THE NEW PLANT

This new Bouvardia originated as a seedling selected from offspring of the breeding stock plant Bridesmaid. The particular seedling was selected by me in 1986 for propagation and testing because of the distinctive flower form and coloration of its blossoms. Specifically, the flower is a lobed tubular corolla which is double. It is cherry pink in color. The selected plant was propagated by me in Roelofarendsveen, Holland through several generations of cutting propagation to establish that its distinctive characteristics hold true from generation to generation and appear to be firmly fixed.

Breeding efforts commenced in 1985 in Roelofarendsveen, Holland where the breeding stock is maintained. My new variety, Roxanne, differs from the mother plant, Bridesmaid, in that it has double flowers, better stem quality, and a longer vase life.

DESCRIPTION OF THE DRAWING

This new variety of the Bouvardia plant is illustrated by the accompanying photograph which shows a blooming cyme of the plant with buds and flowers in various stages of opening.

DESCRIPTION OF THE NEW PLANT

The following is a detailed description of my new Bouvardia plant with color designations according to The National Bureau of Standards, Standard Reference Material, #2107, comprising the ISCC-NBS Centroid Color Charts and NBS Special Publication, #440.

THE PLANT

Origin: Seedling.
Parentage: Seed parent.
Classification: Rubiaceae family.
Form: A vigorously growing small shrub with leaves arranged opposite and flowers in terminal cymes.
Height: Up to 80.0 cm.
Growth: Vigorous.
Root stock: Rhizome.
Foliage:
- *Quantity.*—Many.
- *Number of leaves.*—10–15 per stem.
- *Size of leaf.*—About 7.5 cm.
- *Shape of leaf.*—Lanceolate.
- *Texture.*—Smooth.
- *Color:* Upper Side: Green. Under Side: Green.

THE BUD

Form: Flask-shaped.
Size: Small.
- *Diameter.*—About 0.75 cm.
- *Length.*—About 2.5 cm.

Peduncle:
- *Length.*—About 8.0 cm.
- *Texture.*—Smooth.
- *Form.*—Erect.

THE FLOWER

Blooming habit: Continuously year-round.
Flower size:
- *Diameter.*—About 1.5–2.0 cm.
- *Depth.*—About 2.5 cm.

Borne: Terminal cymes.
Shape: Lobed tubular corolla.
Petalage:
- *Number of Petals.*—Eight - Twelve.
- *Arrangement.*—Two to three concentric circles of four arranged alternately.
- *Form.*—Elliptical.
- *Texture.*—Smooth.
- *Appearance.*—Satiny.

Color: Outer petals: Deep pink (No. 3). Inside petals: Deep pink (No. 3) with a white (No. 263) heart.
Persistence: The flowers hang on and dry.
Main stem or stalk:
- *Length.*—Up to 80.0 cm.
- *Color.*—Green.
- *Character.*—Sturdy and erect.

Lasting quality of flower: About 25 days. As a cut flower 14 days.

REPRODUCTIVE ORGANS

Stamens:
- *Number.*—Four.
- *Arrangement.*—Alternate with corolla lobes.

Anthers:
- *Size.*—About 0.25 cm.
- *Color.*—White (No. 263).

Filaments:
- *Length.*—About 1.0 cm.
- *Color.*—White (No. 263).
- *Pollen.*—Black (No. 267).

Pistils:
- *Number.*—One.
- *Styles.*—Length: About 1.0 cm. Color: White (No. 263).

Fruit:

*Shape.*—Loculicidal capsule, seeds winged.

*Color.*—Brown.

This plant is particularly noted for the distinctive coloration and form of its flowers, which coloration and form does not clearly resemble that of any other Bouvardia plant previously known to me.

I claim:

1. A new and distinctive Bouvardia cultivar, substantially as herein shown and described, characterized by the distinctive coloration and form of its profusely blooming flowers.

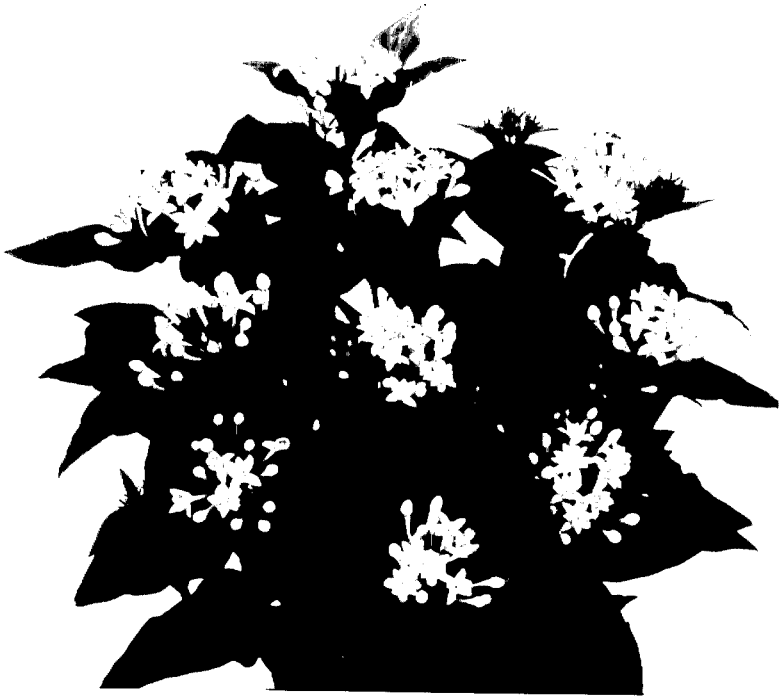

* * * * *